(12) United States Patent
Stinson

(10) Patent No.: US 7,553,325 B2
(45) Date of Patent: *Jun. 30, 2009

(54) BIOABSORBABLE MARKER HAVING RADIOPAQUE CONSTITUENTS

(75) Inventor: Jonathan S. Stinson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/635,114

(22) Filed: Aug. 6, 2003

(65) Prior Publication Data

US 2004/0111149 A1 Jun. 10, 2004

Related U.S. Application Data

(62) Division of application No. 09/748,474, filed on Dec. 26, 2000, now Pat. No. 6,626,936, which is a division of application No. 08/904,951, filed on Aug. 1, 1997, now Pat. No. 6,174,330.

(51) Int. Cl.
*A61F 2/06* (2006.01)
(52) U.S. Cl. ............... 623/1.34; 623/1.15; 623/23.7
(58) Field of Classification Search ................ 623/1.15, 623/1.34, 23.7, 23.71; 606/191, 198
See application file for complete search history.

(56) References Cited

U.S. PATENT DOCUMENTS

| 3,297,033 | A | * | 1/1967 | Schmitt et al. ............ 606/230 |
|---|---|---|---|---|
| 3,918,455 | A | * | 11/1975 | Coplan ..................... 606/225 |
| 4,202,349 | A | | 5/1980 | Jones |
| 4,447,239 | A | | 5/1984 | Krütten |
| 4,475,972 | A | | 10/1984 | Wong |
| 4,655,771 | A | | 4/1987 | Wallsten |
| 4,681,110 | A | | 7/1987 | Wiktor |
| 4,693,237 | A | | 9/1987 | Hoffman et al. |
| 4,722,344 | A | | 2/1988 | Cambron et al. |
| 4,738,740 | A | | 4/1988 | Pinchuk et al. |
| 4,787,391 | A | | 11/1988 | Elefteriades |
| 4,954,126 | A | | 9/1990 | Wallsten |
| 4,968,317 | A | | 11/1990 | Törmälä et al. |
| 5,015,183 | A | | 5/1991 | Fenick |
| 5,024,232 | A | | 6/1991 | Smid et al. |

(Continued)

FOREIGN PATENT DOCUMENTS

CA 2238784 2/1999

(Continued)

OTHER PUBLICATIONS

Bicomponent vascular grafts consisting of synthetic absorbable fibers. 1. In Vitro Study, Tarng-Jenn Yu and C.C. Chu, Journal of Biomedical Materoa's Research, vol. 27, 1329-1339 (1993).

(Continued)

*Primary Examiner*—Paul Prebilic
(74) *Attorney, Agent, or Firm*—Fish & Richardson P.C.

(57) ABSTRACT

A temporary bioabsorbable-radiopaque marker for use on an implantable endoprosthesis. The bioabsorbable-radiopaque marker is adapted to be disposed on or adjacent an implantable endoprosthesis in a body lumen for a predetermined amount of time until the bioabsorbable and radiopaque materials are absorbed or dispersed in the body.

30 Claims, 13 Drawing Sheets

U.S. PATENT DOCUMENTS

| | | | |
|---|---|---|---|
| 5,026,377 A | 6/1991 | Burton et al. | |
| 5,047,050 A | 9/1991 | Arpesani | |
| 5,059,211 A | 10/1991 | Stack et al. | |
| 5,061,275 A | 10/1991 | Wallsten et al. | |
| 5,085,629 A | 2/1992 | Goldberg et al. | |
| 5,116,360 A | 5/1992 | Pinchuk et al. | |
| 5,133,660 A | 7/1992 | Fenick | |
| 5,133,742 A | 7/1992 | Pinchuk | |
| 5,160,341 A | 11/1992 | Brenneman et al. | |
| 5,163,951 A | 11/1992 | Pinchuk et al. | |
| 5,177,170 A | 1/1993 | Sarpeshkar et al. | |
| 5,201,757 A | 4/1993 | Heyn et al. | |
| 5,203,777 A | 4/1993 | Lee | |
| 5,229,431 A | 7/1993 | Pinchuk | |
| 5,256,158 A | 10/1993 | Tolkoff et al. | |
| 5,306,286 A | 4/1994 | Stack et al. | |
| 5,320,602 A | 6/1994 | Karpiel | |
| 5,346,981 A | 9/1994 | Sarpeshkar et al. | |
| 5,354,257 A | 10/1994 | Roubin et al. | |
| 5,366,504 A | 11/1994 | Andersen et al. | |
| 5,370,691 A * | 12/1994 | Samson | 623/1.22 |
| 5,376,376 A * | 12/1994 | Li | 424/443 |
| 5,405,402 A | 4/1995 | Dye et al. | |
| 5,415,546 A | 5/1995 | Cox, Sr. | |
| 5,419,760 A | 5/1995 | Narcisco, Jr. | |
| 5,423,849 A * | 6/1995 | Engelson et al. | 606/191 |
| 5,423,885 A | 6/1995 | Williams | |
| 5,429,617 A | 7/1995 | Hammersmark et al. | |
| 5,433,727 A | 7/1995 | Sideris | |
| 5,441,517 A * | 8/1995 | Kensey et al. | 606/213 |
| 5,464,450 A | 11/1995 | Buscemi et al. | |
| 5,464,650 A | 11/1995 | Berg et al. | |
| 5,478,352 A | 12/1995 | Fowler | |
| 5,484,444 A | 1/1996 | Braunschweiler et al. | |
| 5,498,227 A | 3/1996 | Mawad | |
| 5,500,013 A | 3/1996 | Buscemi et al. | |
| 5,527,337 A | 6/1996 | Stack et al. | |
| 5,527,354 A | 6/1996 | Fontaine et al. | |
| 5,545,208 A | 8/1996 | Wolff et al. | |
| 5,551,954 A | 9/1996 | Buscemi et al. | |
| 5,556,413 A | 9/1996 | Lam | |
| 5,591,172 A | 1/1997 | Bachmann et al. | |
| 5,591,222 A | 1/1997 | Susawa et al. | |
| 5,591,224 A | 1/1997 | Schwartz et al. | |
| 5,591,226 A | 1/1997 | Trerotola et al. | |
| 5,603,722 A * | 2/1997 | Phan et al. | 623/1.18 |
| 5,609,627 A | 3/1997 | Goicoechea et al. | |
| 5,624,411 A | 4/1997 | Tuch | |
| 5,628,755 A | 5/1997 | Heller et al. | |
| 5,628,787 A * | 5/1997 | Mayer | 623/1.15 |
| 5,628,788 A | 5/1997 | Pinchuk | |
| 5,630,840 A | 5/1997 | Mayer | |
| 5,632,771 A * | 5/1997 | Boatman et al. | 623/1.15 |
| 5,645,559 A | 7/1997 | Hachtman et al. | |
| 5,653,747 A | 8/1997 | Dereume | |
| 5,662,703 A | 9/1997 | Yurek et al. | |
| 5,670,161 A | 9/1997 | Healy et al. | |
| 5,674,277 A | 10/1997 | Freitag | |
| 5,674,286 A | 10/1997 | D'Alessio et al. | |
| 5,675,146 A * | 10/1997 | Williams et al. | 250/256 |
| 5,676,146 A * | 10/1997 | Scarborough | 600/431 |
| 5,683,449 A | 11/1997 | Marcade | |
| 5,697,969 A | 12/1997 | Schmitt et al. | |
| 5,700,285 A | 12/1997 | Myers et al. | |
| 5,716,397 A * | 2/1998 | Myers | 623/2.36 |
| 5,718,159 A * | 2/1998 | Thompson | 87/33 |
| 5,718,397 A * | 2/1998 | Stevens | 242/608.8 |
| 5,725,517 A | 3/1998 | DeBusk | |
| 5,725,567 A | 3/1998 | Wolff et al. | |
| 5,725,572 A | 3/1998 | Lam et al. | |
| 5,741,327 A | 4/1998 | Frantzen | |
| 5,756,127 A * | 5/1998 | Grisoni et al. | 424/489 |
| 5,762,265 A * | 6/1998 | Kitamura et al. | 236/51 |
| 5,762,625 A * | 6/1998 | Igaki | 604/8 |
| 5,824,042 A | 10/1998 | Lombardi et al. | |
| 5,843,158 A | 12/1998 | Lenker et al. | |
| 5,888,201 A * | 3/1999 | Stinson et al. | 623/1.2 |
| 5,980,564 A | 11/1999 | Stinson | |
| 6,174,329 B1 * | 1/2001 | Callol et al. | 623/1.34 |
| 6,174,330 B1 | 1/2001 | Stinson | |
| 6,183,508 B1 * | 2/2001 | Stinson et al. | 623/1.2 |
| 6,245,103 B1 | 6/2001 | Stinson et al. | |
| 6,340,367 B1 | 1/2002 | Stinson | |
| 6,626,936 B2 * | 9/2003 | Stinson | 623/1.15 |
| 2003/0204248 A1 | 10/2003 | Murphy | |

FOREIGN PATENT DOCUMENTS

| | | |
|---|---|---|
| EP | 0183372 A1 | 6/1986 |
| EP | 0615769 A1 | 9/1994 |
| EP | 0679372 A2 | 11/1995 |
| EP | 0709068 A2 | 5/1996 |
| EP | 0689807 A3 | 8/1996 |
| EP | 0 756 853 | 2/1997 |
| EP | 0775472 A2 | 5/1997 |
| EP | 0894503 A3 | 2/1999 |
| WO | WO 80/02641 | 12/1980 |
| WO | WO 90/01969 | 3/1990 |
| WO | WO 90/04982 | 5/1990 |
| WO | WO 91/10766 | 7/1991 |
| WO | 91/12779 | 9/1991 |
| WO | WO 92/16166 | 10/1992 |
| WO | WO 94/06372 | 3/1994 |
| WO | WO 94/06373 | 3/1994 |
| WO | WO 96/05872 | 2/1996 |
| WO | WO 96/40000 | 12/1996 |
| WO | 97/13475 | 4/1997 |
| WO | WO 97/11724 | 4/1997 |
| WO | WO 98/18408 | 5/1998 |

OTHER PUBLICATIONS

Biomedical Applications of Synthetic Biodegradable Polymers, Edited by Jeffrey O. Hollinger, D.D.S., Ph.D., CRC Press, p. 21.

Development of a Polymer Endovascular Prosthesis and Its Implantation in Porcine Arteries, William J. Van der Giessen, M.D., et al., Journal of Interventional Cardiology, vol. 5, No. 3, 1992, pp. 175-185.

Role of Polymers in improving the results of stenting in coronary arteries, Tao Peng, et al., Biomaterials 1996, vol. 17, No. 7, pp. 685-694.

Bioabsorbable, Drug-Eluting, Intracoronary Stents: Design and Future Applications, R.S. Schwartz, et al., Coronary Stents (1992), pp. 135-154.

Ten Years of Stenting: What Next!, Ulrich Sigwart, M.D., FRCP, FACC, FESC, Journal of Interventional Cardiology, vol. 10, No. 2, pp. 195-205.

Biocompatibility of solid poly (ortho ester), M. Ekholm, et al., Journal of Materials Science: Materials in Medicine 8, (1997), pp. 265.

The Polymer Stent, Jean-François Tanguay, et al., Endoluminal Stenting, pp. 216-225.

Studies on a new radiopaque polymeric biomaterial, A. Benzina, M.A.B. Kruft, F. Bar, F.H. van der Veen, C.W. Bastiaansen, V. Heijnen, C. Reutelingsperger, and L.H. Koole, Biomaterials 1994, vol. 15 No. 14, pp. 1122-1128.

Deformation Characteristics of a Bioabsorbable Intravascular Stent, C. Mauli Agrawal, Ph.D., PE. and Howard G. Clark, Ph.D., Investigative Radiology, Dec. 1992, vol. 27, pp. 1020-1024.

Studies on radio-opaque polymeric biomaterials with potential applications to endovascular prostheses, M. Kruft, A. Benzina, R. Blezer, and L. Koole, Biomaterials 1996, vol. 17, No. 18, pp. 1803-1812.

Gianturco-Roubin Flex-Stent GRII, M-D-D-I Report—"The Gray Sheet", Mar. 4, 1996.

Synthetic Biabsorbable Polymers, Thomas H. Barrows, Ph.D., High Performance Biomaterials, Szycher ed., pp. 243-257.

Wound Closure Biomaterials and Devices, C.C. Chu, J.A. von Fraunhofer, and H.P. Greisler, CRC Press, Boca Raton, FL, 1997, pp. 131-235.

In Vitro Degradation of Polyactides Depending on Different Processes, M. Dauner, E. Muller, B. Wagner, and H. Planck, Degradation Phenomena on Polymeric Biomaterials, H. Planck, M. Dauner, M. Renardy (eds), Springer-Verlag, Berlin, 1992, pp. 107-122.

Long-term in vivo degradation and bone reaction to various polylactides, P. Mainil-Varlet, B. Rahn, and S. Gogolewski, Biomaterials 1997, vol. 18, No. 3, pp. 257-266.

Current Status of Biodegradable Stents, J.F. Tanguay, M.D., J.P. Zidar, M.D., H.R. Phillips, III, M.D., and R. S. Stack, M.D., Cardiology Clinics, vol. 12, No. 4, Nov. 1994, pp. 699-713.

Perspectives on the In Vivo Responses of Biodegradable Polymers, James M. Anderson, M.D., Ph.D., CRC Press Inc., (1995) pp. 223-233, 1995.

New Methods of Drug Delivery, Robert Langer, Science vol. 249, pp. 1527-1533.

Enhancement of the Mechanical Properties of Polyactides by solid-state extrusion, Walter Weiler and Sylwester Gogolewski, Biomaterials 17 (1996), pp. 529-535.

The Physics of Radiology, H.E. Johns and J.R. Cunningham, pp. 135-142.

The Physics of Diagnostics Imagery, D. Dowsett et al., Champman Hall Medical, 1998, pp. 107-112.

CRC Handbook of Chemistry and Physics, $73^{rd}$ Edition, D.R. Lide, CRC Press, Inc., 1992, pp. 10-289 and 10-291.

Metals Handbook Desk Edition, H.E. Boyer et al., American Society for Metals 1985, pp. 1.44 to 1.48.

Enhancement of the Mechanical Properties of Polylactides by solid-state extrusion, Walter Weiler and Sylwester Gogolewski, Biomaterials 17 (1996), pp. 529-535.

Advertisement for radiopaque polymers for medical device manufacturing, New England Urethane, Inc.

Advances in Controlled Release Technology: Polymeric Delivery System s for Drugs, Pesticides and Foods: Fundamentals of pH. and Temperature-Sensitive Polymers, Nicholas A. Peppas, pp. 32-45, (Jul. 1994).

U.S. Appl. No. 08/598,751 entitled "Titanium Alloy Self-Expanding Stent", which is commonly owned by the assignee of the above-captioned application, filed Feb. 8, 1996.

Notice of Opposition Against European Patent No. EP 0894503.

Translation of Notice of Opposition Against European Patent No. EP 0894503.

* cited by examiner

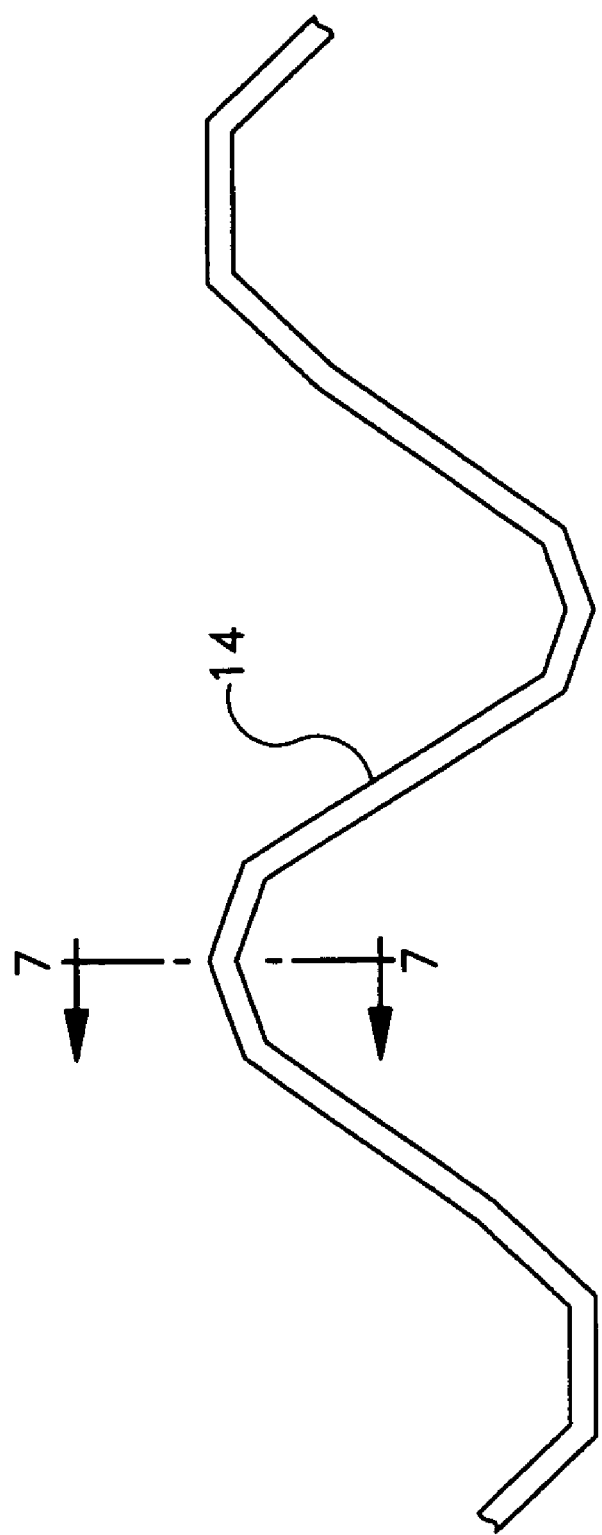

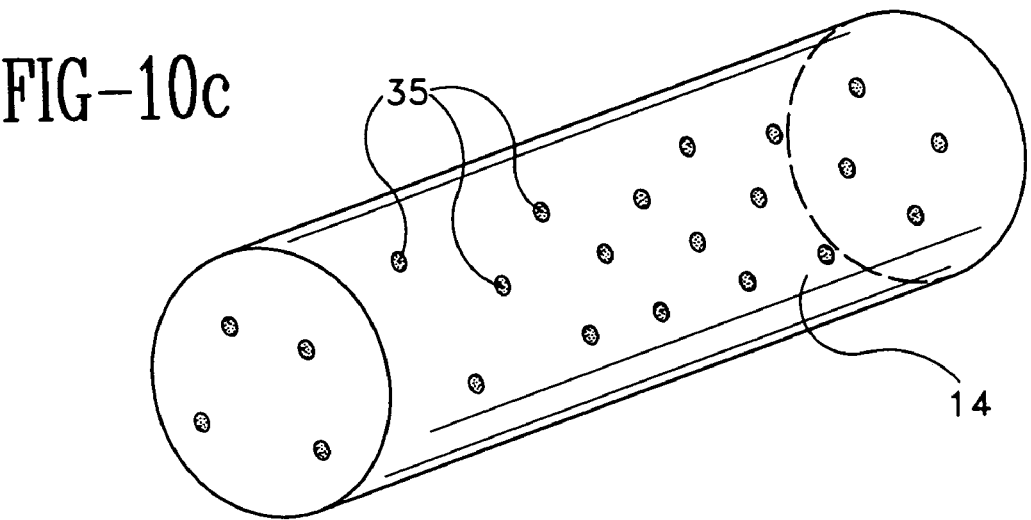
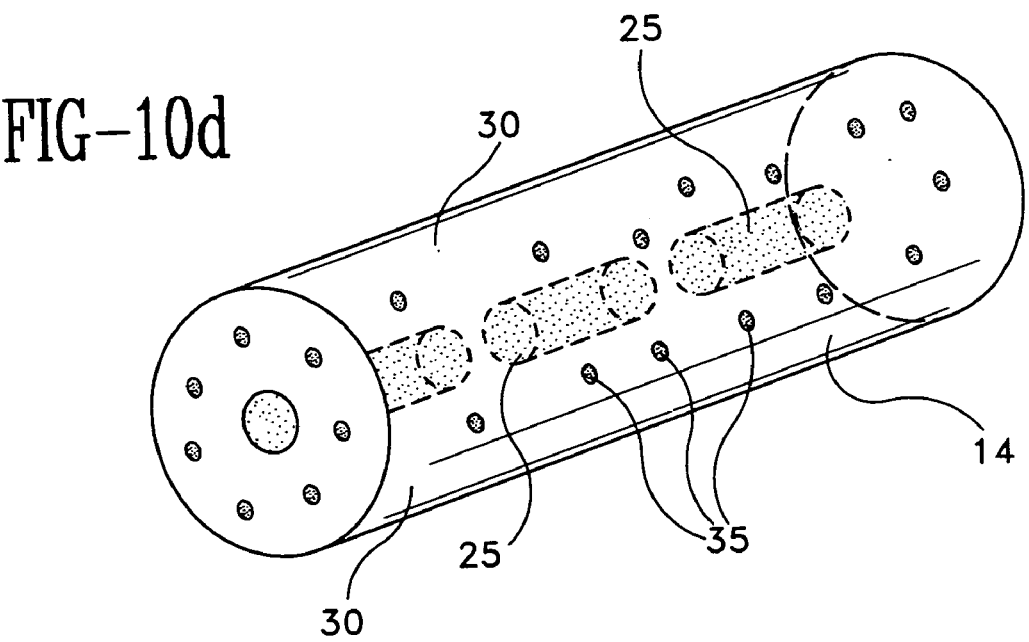

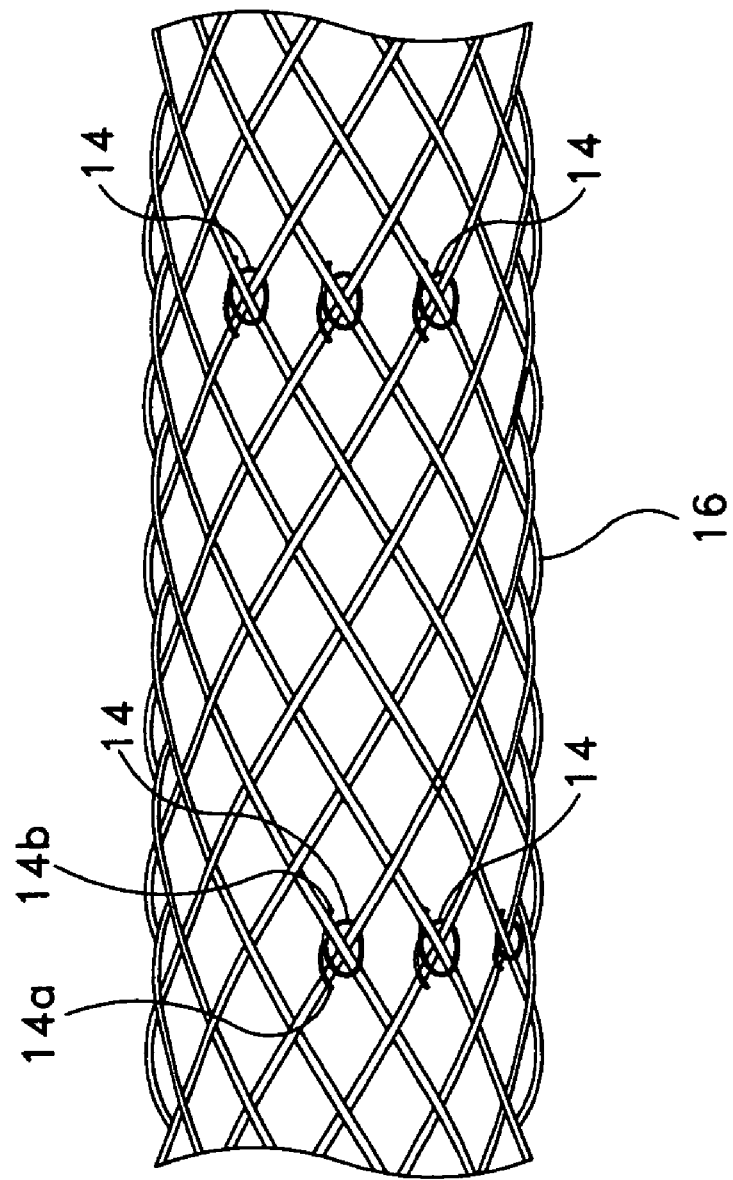

BIOABSORBABLE MARKER HAVING RADIOPAQUE CONSTITUENTS

BACKGROUND OF THE INVENTION

This application is a divisional of U.S. application Ser. No. 09/748,474, filed Dec. 26, 2000, now U.S. Pat. No. 6,626,936, which is a divisional of U.S. application Ser. No. 08/904,951, filed Aug. 1, 1997, now U.S. Pat. No. 6,174,330. The disclosures of these applications are incorporated by reference.

This invention relates generally to a bioabsorbable marker having radiopaque constituents "bioabsorbable-radiopaque marker" for use on an implantable endoprosthesis such as a stent. The bioabsorbable marker includes dispersable radiopaque constituents which are not bioabsorbable or degradable, but are excreted from the body or stored in the body.

Implantable endoprostheses including stents, stent-grafts, and grafts are used in percutaneous transluminal coronary angioplasty and in other medical procedures to repair and support diseased or damaged arteries and body lumens. Grafts are implanted to cover or bridge leaks or dissections in vessels. Stent-grafts are stents which generally have a porous coating attachment. Unsupported grafts are porous tubes which are typically implanted by surgical cut-down.

In order to visualize the passage and placement of the implantable endoprosthesis in arteries and body lumens, many surgical procedures are performed with the aid of fluoroscopic angiography. The surgical delivery device and implantable endoprosthesis may be visualized if they are radiopaque and offer radiographic contrast relative to the body. For example, X-ray radiation may be used to visualize surgical delivery devices and deployment of the implant in the body. Also, radiographic contrast solution may be injected into the body lumen so that the lumen may be seen in the fluoroscopic image.

In order for the Implantable endoprosthesis to be radiopaque, it must be made from a material possessing radiographic density higher than surrounding host tissue and have sufficient thickness to affect the transmission of x-rays to produce contrast in the image. Reference is made to the clad composite stent shown in U.S. Pat. No. 5,630,840. An implantable endoprosthesis may be made of metals including tantalum, or platinum having relatively high radiographic densities. Other metals such as stainless steel, superalloys, nitinol, and titanium having lower radiographic densities may also be used. Reference is made to implantable devices shown in U.S. Pat. Nos. 4,655,771; 4,954,126; and 5,061,275.

An implantable polymeric endoprosthesis is generally radiolucent and does not possess sufficient radiographic density to be easily imaged by fluoroscopy. To improve the imaging of such polymeric materials, polymers may be mixed with radiopaque filler materials prior to molding or extruding in order to enhance the radiographic density. However, a disadvantage of using fillers with polymers is that changes in the properties of the polymer may occur. For example, the additions of fillers. may reduce the strength or ductility of the polymer.

There is a need for an improved bioabsorbable-radiopaque marker for use in medical devices, particularly, in temporary medical devices having low radiopacity. The need to improve the radiopacity of a relatively low radiopaque implantable endoprosthesis or to improve imaging in low radiopaque conditions is particularly important for surgery, micro-surgery, neuro-surgery, and conventional angioplasty procedures performed under fluoroscopy. Physicians are constantly being challenged to place small implants at specific intraluminal locations. Various devices having radiopacity are known in the art such as shown in U.S. Pat. Nos. 4,447,239; 5,354,257; and 5,423,849.

All documents cited herein, including the foregoing, are incorporated herein by reference in their entireties for all purposes.

SUMMARY OF THE INVENTION

Accordingly, there is a need for bioabsorbable-radiopaque markers for use on implantable endoprostheses in order to improve radiopacity and the locatability of an endoprosthesis during various medical procedures. Providing temporary radiopacity is especially advantageous for implantable endoprostheses having little or no radiopacity. The bioabsorbable-radiopaque markers allow radiographic identification of one or more locations of interest on an implantable endoprosthesis. Bioabsorbable-radiopaque markers in the fabric or covering materials of an implantable endoprosthesis are advantageous for indicating the location of the fabric or covering during implantation.

Alternative uses include threading the markers: adjacent a helical strand in the implantable endoprosthesis; circumferentially around the implantable endoprosthesis; or in a straight line in the axial direction of the implantable endoprosthesis. One or more bioabsorbable-radiopaque markers may be used on the implantable endoprosthesis having little or no radiopacity. After implantation, the bioabsorbable-radiopaque marker may be absorbed, dissolved, or excreted from the body so as not to effect the function of the endoprosthesis.

A disadvantage of certain permanent radiopaque markers is that they may compromise structural integrity, may not be biocompatible or biostable, and may be more thrombogenic than the implantable endoprosthesis.

The bioabsorbable-radiopaque marker of the present invention advantageously allows most any implantable endoprosthesis to have temporary radiopacity over a predetermined portion of its structure, and advantageously assists with proper positioning and locatability of the implantable endoprosthesis in a body lumen.

Use of the bioabsorbable-radiopaque marker is advantageous because the radiopaque property may be present only for a desired time period on an implantable endoprosthesis. For instance, once the implantable endoprosthesis is implanted, it may be more desirable to image with techniques such as ultrasound, magnetic resonance, and endoscopy and to avoid further radiation exposure to the patient. As the bioabsorbable polymer degrades, radiopaque material simultaneously or subsequently disperses into the body. The dispersion of the radiopaque material from the marker results in a loss of radiopacity in the marker. A predetermined rate of release of the radiopaque material may be designed into the bioabsorbable marker based on degradation of the polymer in the body or the design of the marker structure.

The bioabsorbable material in the bioabsorbable-radiopaque markers may include polymers or copolymers such as polylactide [poly-L-lactide (PLLA), poly-D-lactide (PDLA)], polyglycolide, polydioxanone, polycaprolactone polygluconate, polylactic acid-polyethylene oxide copolymers, modified cell lose, collagen, polyhydroxybutyrate), polyanhydride, polyphosphoester, poly(amino acids), poly(alpha-hydroxy acid) or related copolymers materials, each of which have a characteristic degradation rate in the body. For example, polyglycolide and polydioxanone are relatively fast-bioabsorbing materials (weeks to months) and PLA is a relatively slow-bioabsorbing material (months to yea). For a PLA member, mass degradation is completed with total absorption of the polymer endoprosthesis in about 1.5 to 3 years after implantation.

Bioabsorbable resins such as PLLA, PDLA, PGA and others are commercially available from several sources including PURAC America, Inc. of Lincolnshire, Ill. Radiopaque materials such as barium sulfate and bismuth trioxide are commercially available and compounded with the bioabsorbable resin by New England Urethane, Inc. of North Haven, Conn. The bioabsorbable resin or bioabsorbable-radiopaque resin may be extruded into filament by Albany International Research Co. of Mansfield, Mass.

The bioabsorption rate of the marker may be designed to be fast for applications where acute radiopacity is desired such as during positioning and placement of the implant. Alternatively, the bioabsorption rate may be designed to be slower for applications where the implant must be radiographically imaged for at least a portion of its functional time, for example, in implants where healing may take months. Other bioabsorption rates are also possible. The bioabsorption rate of the marker may be tailored by controlling the type of bioabsorbable polymer; chemical composition of the bioabsorbable polymer; molecular weight of the bioabsorbable polymer; thickness and density of the bioabsorbable polymer; surface area of the marker, exit area for the radiopaque material, and design of the marker structure.

The degradation products from the bioabsorbable marker and the dispersed radiopaque material are metabolized, excreted, or stored by the body. Metabolism is the chemical process in living cells by which energy is provided for vital processes and activities and new material is assimilated to repair the waste. It is the sum of the processes by which a particular substance is handled in the living body. Excretion is separation and elimination or discharge from the blood or tissues of useless, superfluous, or harmful material that is eliminated from the body.

The biocompatibility of absorbable polymers during degradation depends upon the rate of accumulation and how well the surrounding tissue or fluid buffers or metabolizes the degradation products. If the products are metabolizable, the rate at which this will occur is dependent upon the blood circulation in the tissue. A well-vascularized lumen wall could buffer and metabolize degradation products as they are released from the implant. This biological process is important to minimize adverse tissue reaction to the degrading implant.

The degradation products from PLLA and PGA are lactic and glycolic acid, respectively, which are normally present in the human body. The acids are metabolized by cells around the implant. The metabolization process is a citrate cycle which converts the acids to carbon dioxide which is respirated out of the body.

The radiopaque agents added to the bioabsorbable marker are generally insoluble in the body and thus are not metabolizable. If these materials are trapped within tissue, the host generally reacts by encapsulation and acceptance of the biologically inactive particles. If the material is released from the implant into systemic circulation, it will migrate with fluid flow until being excreted or collected and stored by organs or tissue. The idea is to only have small amounts of the radiopaque substances in the implant by incorporating the discrete bioabsorbable-radiopaque marker rather than to load the entire implant with the radiopaque material. Minimization of the amount of radiopaque material which will be liberated from the marker upon absorption of the polymer must be considered when determining the loading percentage based on radiographic and mechanical properties.

To be radiopaque, the markers should include material having atomic elements of sufficiently high atomic number and be of sufficient thickness to provide sufficient radiopacity for imaging. The bioabsorbable-radiopaque marker may have one or more hollow, cavity, or porous portions wherein radiopaque material may be disposed.

Attenuation is the change in the number of photons in the incident x-ray beam due to the interaction with an absorber. To image an object implanted in the body, it would be desirable to have the object attenuate x-rays more than body tissue, bone, and fat so that the difference in contrast will be obvious in a radiograph. The difficulty in selecting a radiopaque material for surgical implants is that the material must have desirable radiographic characteristics and biocompatibility.

In order to make an implant more radiopaque, a substance which absorbs more x-rays can be deposited on or mixed in with the implant material. If the implant absorbs more x-rays than the surrounding medium (for example tissue in the body), it will be visible as a sharp change in contrast on an x-ray film or fluoroscopy image.

The fraction of x-ray energy transmitted through the absorber is quantitatively predicted by the following equation described in *The Physics of Radiology*, Fourth Ed., H. Johns, J. Cunningham, 1983, pp. 137-142.

$N = N_0 e^{-\mu x}$ $N$ = number of photons transmitted through x $N_0$ = number of photons in the incident beam $\mu$ = linear attenuation coefficient of the absorber x = absorber thickness $N/N_0$ would be the fraction of incident x-ray energy that is transmitted through the absorber. A more radiopaque material would have a lesser fraction of transmitted energy than a more radiolucent material. Therefore, to enhance the radiopacity of a material, such as the marker material, it would be desirable to select a material with high x-ray absorbing capability to minimize the fraction of transmitted energy. This radiopacity capability is proportional to the linear attenuation coefficient and the thickness of the absorber material. The higher the attenuation coefficient of the absorber material for a given thickness, the more radiopaque the absorber will be. The attenuation produced by an absorber is dependent upon the number of electrons and atoms present in the absorber. One way of quantifying this absorption characteristic is with the atomic attenuation coefficient which is directly proportional to the linear attenuation coefficient and the atomic number of the absorber element. Radiopacity is therefore generally proportional to the atomic number (number of electrons in the atom) of the material. Candidate materials for enhancing the radiopacity of surgical implants would have higher atomic numbers than the elements present in the body and would have to be biocompatible. The atomic number must be sufficiently high so that relatively small thickness of absorber material can be used in the body. Reference is also made to linear attenuation coefficient described in U.S. Pat. No. 5,628,787. Reference is made to Table 1 which describes a number of elements and their respective atomic numbers and certain linear attenuation coefficients.

TABLE 1

| Element or Material | Atomic Number or Effective Atomic Number | Linear Attenuation Coefficient at 50 KeV, cm$^{-1}$ |
|---|---|---|
| hydrogen | 1 | .000028 |
| carbon | 6 | .417 |
| fat | 6.46 | .193 |
| water | 7.51 | .2245 |
| muscle | 7.64 | .233 |
| air | 7.78 | .000247 |
| nitrogen | 7 | .000228 |
| oxygen | 8 | .000280 |
| bone | 12.31 | .573 |
| titanium | 22 | 5.46 |
| iron | 26 | 15.42 |
| cobalt | 27 | 18.94 |
| bromine | 35 | 13.29 |
| zirconium | 40 | 40.04 |
| iodine | 53 | 60.76 |
| barium | 56 | 49.68 |
| tantalum | 73 | 94.95 |
| platinum | 78 | 149.08 |
| gold | 79 | 140.12 |
| lead | 82 | 91.17 |
| bismuth | 83 | 82.12 |
| iridium | 77 | 151.53 |
| nickel | 28 | 21.98 |

The elements hydrogen, oxygen, carbon, and nitrogen are commonly found in the body and in polymers, so elements with higher atomic numbers than these should enhance the radiopacity of a polymer implant or marker. Tantalum, zirconium, titanium, barium, bismuth, and iodine are known to be non-toxic in certain concentrations and thus are candidate elements for enhancing radiopacity of a polymer marker in an implant. These elements can be added to the polymer in various loading percentages and the threshold above which the loading causes unsatisfactory changes in the polymer characteristics can be determined through material and device testing. The elements which can be added in quantities sufficient to enhance radiopacity and maintain an acceptable level of polymer properties and which are biocompatible could be utilized in markers. The biocompatible elements with a range of atomic numbers of from about 22 to about 83 and having linear attenuation coefficients in the range of from about 5.46 to about 151.53 cm$^{-1}$ at 50 KeV should provide enough enhancement in radiopacity without excessive thickness being necessary to be useful in markers. These elements would include at least titanium, vanadium, chromium, iron, cobalt, nickel, copper, bromine, zirconium, niobium, molybdenum, silver, iodine, barium, tantalum, tungsten, platinum, gold, and bismuth. The preferred metallic elements for biocompatibility and radiopacity are titanium, zirconium, tantalum, and platinum. The preferred organic elements for biocompatibility and radiopacity are bromine, iodine, barium, and bismuth. Especially preferred elements are tantalum, platinum, barium, and bismuth because of their high atomic numbers and biocompatibility (atomic numbers from 56 to 83 and linear attenuation coefficients from about 50 to about 151.53). Tantalum and platinum are used as stent components and barium sulfate and bismuth trioxide are used as radiopaque enhancements for polymer catheters.

The bioabsorbable-radiopaque marker may be integrated into a subassembly or a finished implantable endoprosthesis during manufacture. Radiopaque elongate elements may be braided together with non-radiopaque bioabsorbable elongate elements to form a tubular braided stent, or the bioabsorbable and radiopaque elongate elements may be woven into the finished-braided stent.

The bioabsorbable-radiopaque marker would advantageously add temporary radiopacity to an implantable endoprosthesis such that the temporary marker would not require a medical procedure for removal from the patient.

In sum the invention relates to an implantable endoprosthesis and bioabsorbable-radiopaque marker system including an implantable endoprosthesis adapted to be disposed in a body lumen and at least one marker. The marker having a proximal end, a distal end, and a thickness. The marker including bioabsorbable material and radiopaque material and is disposed on or adjacent the endoprosthesis. The marker is adapted to degrade in vivo whereby the bioabsorbable material is metabolized through or excreted from the body and the radiopaque material is excreted from or stored in the body. The bioabsorbable material may include a polymer or copolymer. The bioabsorbable material may include poly-L-lactide, poly-D-lactide, polyglycolide, polydioxanone, polycaprolactone, and polygluconate, polylactic acid-polyethylene oxide copolymers, modified cellulose, collagen, poly (hydroxybutyrate), polyanhydride, polyphosphoester, poly (amino acids), poly (alpha-hydroxy acid) and combinations thereof. The radiopaque material may have a linear attenuation coefficient of from about 5.46 cm$^{-1}$ at 50 KeV to about 151.53 cm$^{-1}$ at 50 KeV. The marker may have an average thickness of from about 20 microns to about 500 microns and the radiopaque material includes at least one element with an atomic number of from about 22 to about 83. The radiopaque material may include barium sulfate, bismuth trioxide, bromine, iodine, iodide, titanium oxide, zirconium oxide, tantalum, and combinations thereof. The radiopaque material may be an oxide or salt material. One of the bioabsorbable material or radiopaque material may be coated or compounded with the other and the radiopaque material may have a linear attenuation coefficient of from about 5.46 cm$^{-1}$ at 50 KeV to about 151.53 cm$^{-1}$ at 50 KeV. The marker may have a weight percent of the radiopaque material in the bioabsorbable material of from about 1% to about 80%. The bioabsorbable material may consist of PLLA and the radiopaque material may consist of bismuth trioxide and the weight percent of the bismuth trioxide in the PLLA may be at least about 10%. The bioabsorbable material may consist of PLLA and the radiopaque material may be barium sulfate and the weight percentage of the barium sulfate in the PLLA may be at least about 10%. The marker may substantially degrades in less than about 3 years. "Substantial degradadation of the marker" means that the marker has lost at least 50% of its structural strength. It is preferable that the marker lose about 100% of its structural strength. The bioabsorbable material may consist of polylactide and the radiopaque material may consist of barium sulfate, bismuth trioxide, iodine, iodide, and combinations thereof and the marker substantially degrades in from about 1 year to about 2 years. The bioabsorbable material may include poly-L-lactide, poly-D-lactide, polyglycolide, and combinations thereof and the radiopaque material may include barium sulfate, bismuth trioxide, bromine, iodine, iodide, and combinations thereof and the marker substantially degrades in from about 3 months to about 1 year. The bioabsorbable material may include polyglycolide, polygluconate, polydioxanone, and combinations thereof and the radiopaque material may include barium sulfate, bismuth trioxide, bromine, iodine, iodide, and combinations thereof and the marker substantially degrades in from about 1 week to about 3 months. The marker may be a mono-filament, multi-filament, thread, ribbon, suture, and combinations thereof. The marker may include one or more hollow, cavity, porous, and combinations thereof portions and the radiopaque material may be disposed therein. The marker may have radiopacity for a predetermined amount of time. The endoprosthesis may be a stent, stent-graft, graft, filter, occlusive device, or valve. The endoprosthesis may have a tubular, radially expandable structure and axially flexible structure including a plurality of the elongate elements which are interwoven in a braid-like configuration.

The invention also relates to an implantable endoprosthesis and bioabsorbable-radiopaque marker system including an implantable endoprosthesis adapted to be disposed in a body lumen and at least one elongated marker. The marker is adapted to be disposed on or adjacent the endoprosthesis. The marker includes a proximal end, distal end, thickness, bioabsorbable material, and a radiopaque material having a linear attenuation coefficient of from about 5.46 cm$^{-1}$ at 50 KeV to about 151.53 cm$^{-1}$ at 50 KeV. The marker has at least one hollow, cavity, or porous portion where the radiopaque material may be disposed. The bioabsorbable material at least partially contains the radiopaque material in the marker. The radiopaque material may be a liquid, solid, powder, gel, particle, or combinations thereof.

The invention also relates to a method of marking an implantable endoprosthesis including: disposing at least one elongate marker on or adjacent to at least a portion of an implantable endoprosthesis. The marker is from about 20 weight percent to about 99 weight percent of a bioabsorbable polymer and from about 1 weight percent to about 80 weight percent of a radiopaque material. The radiopaque material includes liquid or particles, the particles having an average diameter less than about 200 microns and a maximum diameter less than about 400 microns. The radiopaque material has a linear attenuation coefficient of from about 5.46 cm$^{-1}$ at 50 KeV to about 151.53 cm$^{-1}$ at 50 KeV; disposing the endoprosthesis and marker in a delivery system; inserting the delivery system in a body lumen; deploying the endoprosthesis and marker from the delivery system into a body lumen; and allowing the polymer to bioabsorb or excrete and the radiopaque material to subsequently or simultaneously at least partially disperses from the endoprosthesis.

The invention also relates to a temporary bioabsorbable-radiopaque marker including a marker having an average thickness less than about 500 microns and consisting of a bioabsorbable material and a radiopaque material, the radiopaque material having a linear attenuation coefficient of from about 5.46 cm$^{-1}$ at 50 KeV to about 151.53 cm$^{-1}$ at 50 KeV. The marker is adapted to be disposed in a body lumen and degrade in vivo. The marker may be elongate and have a proximal end and a distal end.

The invention also relates to a bioabsorbable-radiopaque marker including an elongate element adapted to be disposed in a body lumen and used as a surgical guide, the element including a bioabsorbable material, a radiopaque material, and combinations thereof. The element has a weight percent, W, of the radiopaque material in the bioabsorbable material, and an average thickness, T, over the length of the elongate element. The weight percent, W, is equal to about:

(i) [10+((950×T(measured in mm))−208.5)] ±5 for radiopaque material having atomic weight 20-100;

(ii) ((950×T(measured in mm))−208.5) ±5 for radiopaque material having atomic weight of 100 to 150 up to a maximum of 80 weight percentage; or (iii) [((950×T(measured in mm))−208.5) −10] ±5 for radiopaque material having atomic weight greater than 150. The minimum W is about 1 and the maximum W is about 80.

The invention also relates to a marker including from about 20 weight percent to about 99 weight percent of a bioabsorbable polymer; and from about 1 weight percent to about 80 weight percent of a radiopaque material. The radiopaque material includes at least one of a liquid or particle having an average particle diameter less than about 8 microns and a maximum particle diameter less than about 10 microns. The radiopaque material has a linear attenuation coefficient of from about 5.46 cm$^{-1}$ at 50 KeV to about 151.53 cm$^{-1}$ at 50 KeV. For vascular system. The preferred average particle size is from about 3 microns to about 6 microns and a maximum particle size of 6 microns. For the digestive system, the average particle size may be from about 100 microns to about 150 microns and a maximum particle size of 400 microns.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 6 is a side view of a relatively flexible bioabsorbable-radiopaque marker;

FIGS. 10a-10d are side views of four elongate elements having radiopaque materials therein.

FIG. 11 is a side view illustrating one possible arrangement of discrete bioabsorbable-radiopaque markers disposed on an implantable endoprosthesis;

DETAILED DESCRIPTION OF THE INVENTION

Figure 1:
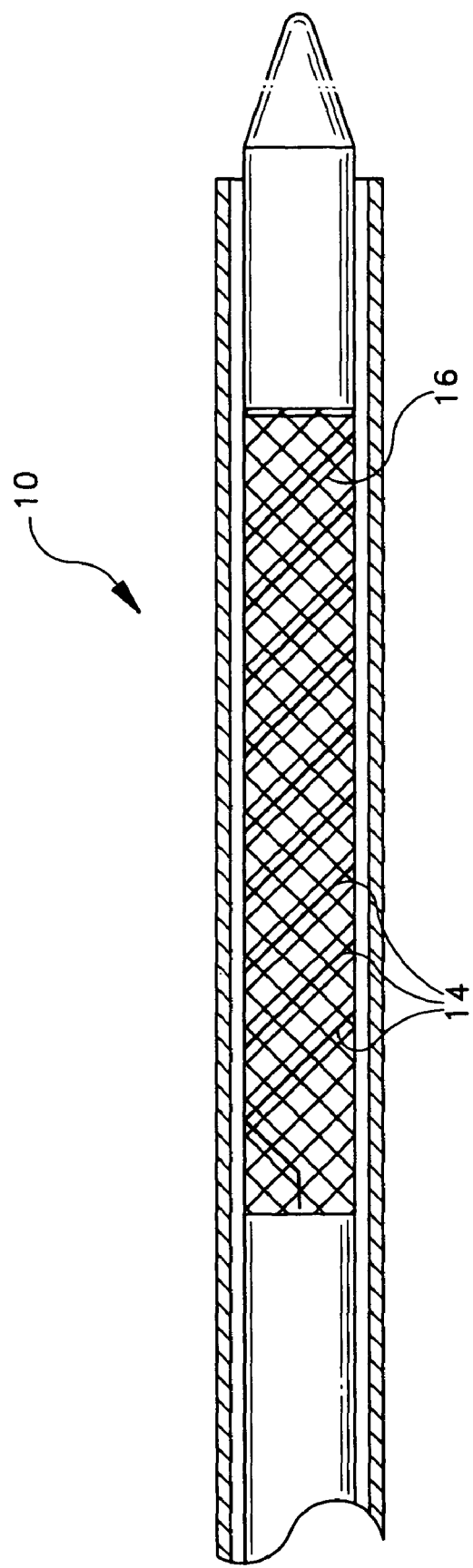
FIG. 1 is a side view of stent delivery system having a bioabsorbable-radiopaque marker disposed on an implantable endoprosthesis.

Reference is made to FIG. 1 illustrating a stent delivery device 10 having one or more bioabsorbable-radiopaque markers 14 disposed in a helical pattern on an implantable endoprosthesis 16. The bioabsorbable-radiopaque marker 14 is disposed on the endoprosthesis 16 preferably before loading the assembly thereof into the outer tube of a delivery device 10. Reference is made to a delivery device shown in U.S. Pat. No. 5,026,377.

Figure 2:
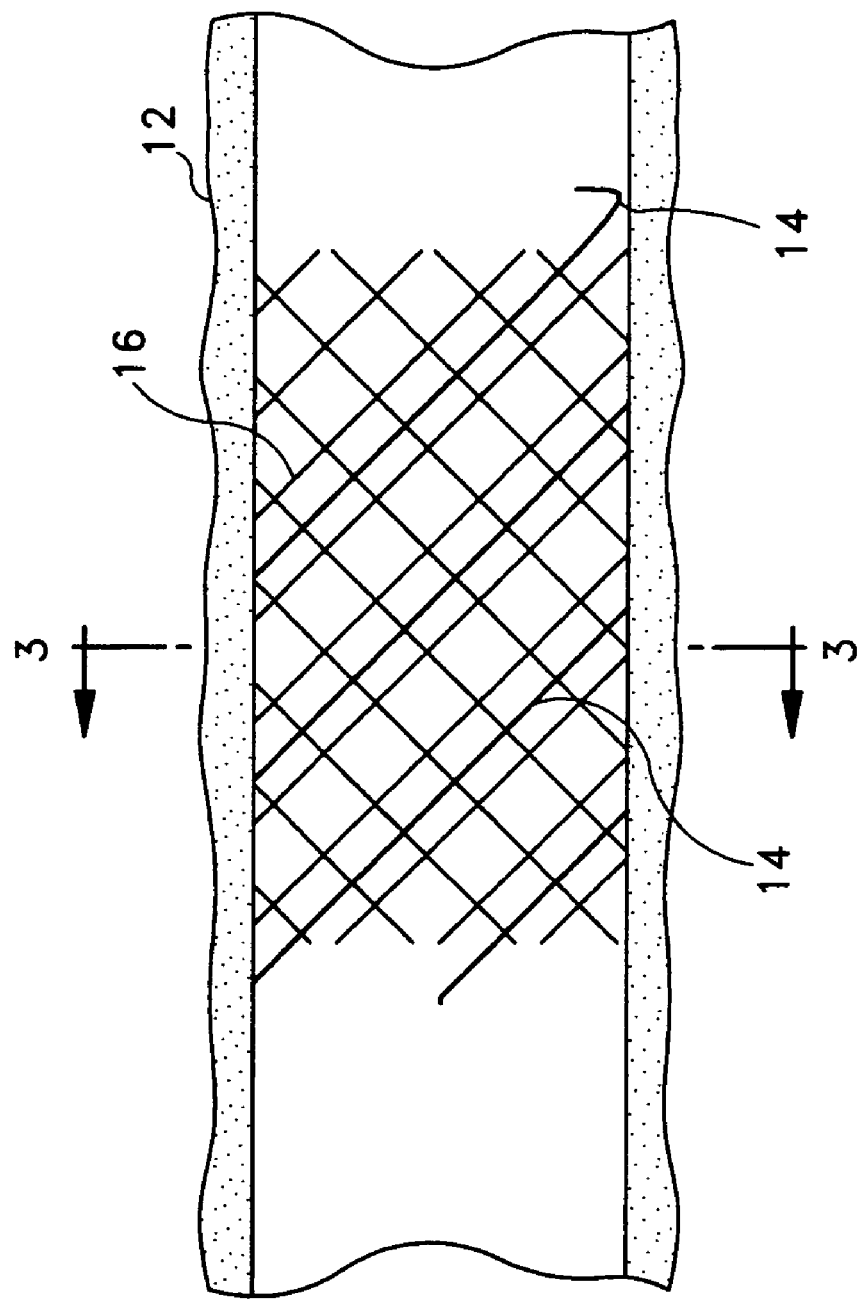
FIG. 2 is a side view of the delivery system and a deployed implantable endoprosthesis in a body lumen.

FIG. 2 illustrates an implantable endoprosthesis 16 having a bioabsorbable-radiopaque markers 14 disposed in a helical pattern thereon in a body lumen 12. Implantable endoprostheses 16 known in the art include stents, stent-grafts, grafts, filters, occlusive devices, valves, and combinations thereof, all may incorporate the bioabsorbable-radiopaque marker 14.

Figure 3C:
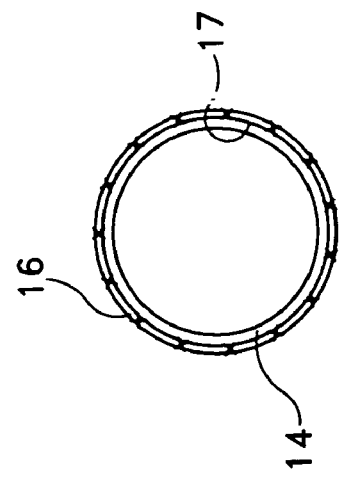
FIGS. 3a, 3b, and 3c are cross-sectional views of three alternative marker dispositions of the bioabsorbable-radiopaque marker on the implantable endoprosthesis at section 3-3 of FIG. 2.
Figure 3B:
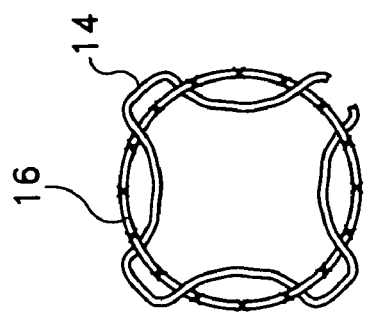
Figure 3A:
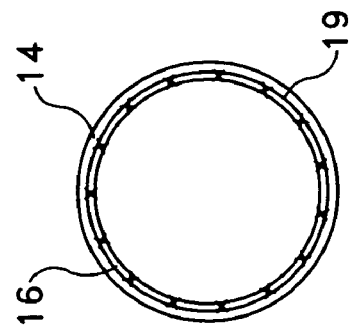

FIGS. 3a-3c illustrate three alternative locations on an implantable endoprosthesis 16 for disposing the bioabsorbable-radiopaque marker. The bioabsorbable-radiopaque marker 14 may be disposed on portions of the inside surface 17, outside surface 19, or be inter-woven or inter-braided about and through the elongated elements of the implantable endoprosthesis 16. The bioabsorbable-radiopaque marker 14 may be disposed on the implantable endoprosthesis 16 in one or more predetermined lengths.

Figure 4:
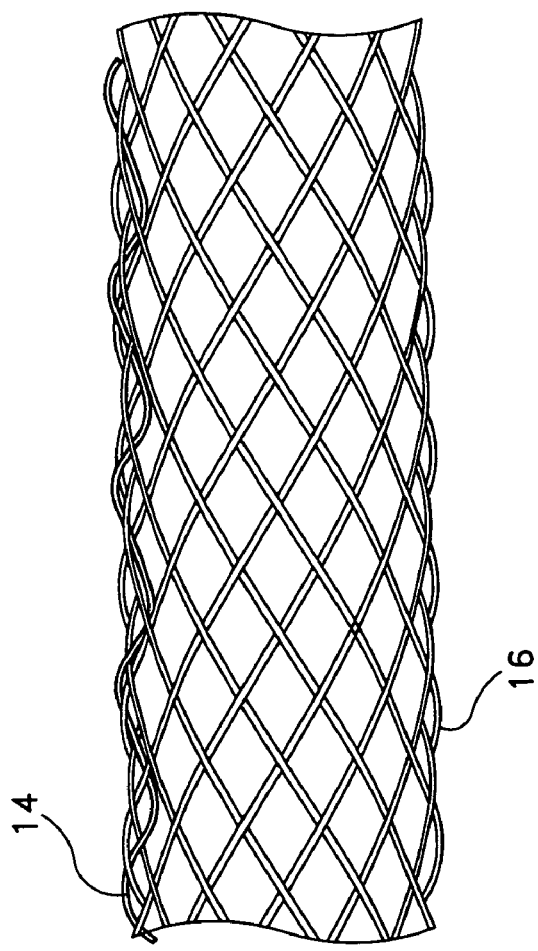
FIG. 4 is a side view of a bioabsorbable-radiopaque marker disposed in a longitudinal pattern on a implantable endoprosthesis.
Figure 5:
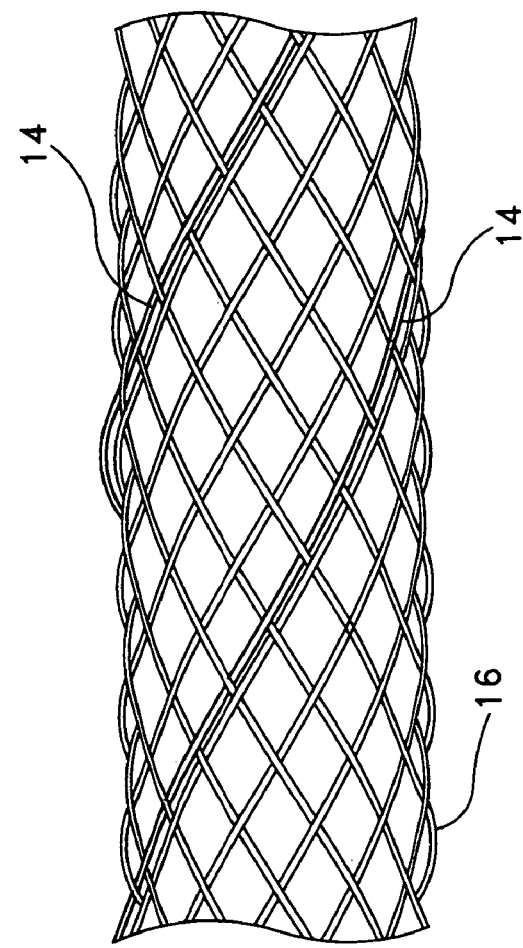
FIG. 5 is a side view of a bioabsorbable-radiopaque marker disposed in a helical pattern on a implantable endoprosthesis.

Reference is made to FIGS. 4 and 5 illustrating the bioabsorbable-radiopaque marker 14 disposed in two alternative patterns on the implantable endoprosthesis 16. FIG. 4 shows the bioabsorbable-radiopaque marker 14 interwoven through the filaments of the endoprosthesis 16 in a relatively longitudinal pattern. Alternatively, the bioabsorbable-radiopaque marker 14 may be interwoven through the filaments of the endoprosthesis 16 in a relatively circumferential pattern. FIG. 5 shows a marker 14 interwoven through the filaments of the endoprosthesis 16 in a relatively helical pattern. Other patterns and dispositions of the bioabsorbable-radiopaque marker 14 on the endoprosthesis 16 are also possible. One or more markers 14 may be temporarily disposed on the implantable endoprosthesis 16 to advantageously provide temporary radiopacity to predetermined locations on the implantable endoprosthesis 16.

As shown in FIGS. 3a and 3c, the bioabsorbable-radiopaque marker 14 may be disposed to one or more surfaces of the implantable endoprosthesis 16 with a relatively weak bioabsorbable adhesive or gelatin.

The bioabsorbable-radiopaque marker 14 may include elongate elements such as a ribbon, thread, filament, suture, or combinations thereof. The bioabsorbable-radiopaque marker 14 may be braided to form a rope or cable.

As the implantable endoprosthesis 16 is deployed from the delivery device 10, the bioabsorbable-radiopaque marker 14 may adjust with the expansion of the implantable endoprosthesis 16, and advantageously provide radiopacity and enhance the viewing of the implantable endoprosthesis 16 position or size during fluoroscopy. Once the implantable endoprosthesis 16 is fully deployed, the delivery device 10 may be removed from the body and the bioabsorbable-radiopaque marker 14 may remain on the implantable endoprosthesis 16 to be bioabsorbed, dissolved, dispersed, or excreted from the body. The bioabsorbable-radiopaque marker 14 may be designed to remain on the implantable endoprosthesis 16 for a predetermined period of time if there is a need for follow-up angiography.

Reference is made to FIG. 6 illustrating a bioabsorbable-radiopaque marker 14 preferably made from a relatively flexible elongate polymeric material including radiopaque material containing at least one element with an atomic number of from about 22 to about 83. The radiopaque material preferably has a linear attenuation coefficient of from about 5.46 $cm^{-1}$ at 50 KeV to about 151.53 $cm^{-1}$ at 50 KeV.

Figure 7A:
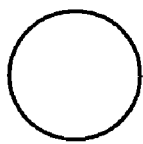
FIGS. 7a-7e are cross-sectional views of five alternative bioabsorbable-radiopaque markers at section 7-7 of FIG. 6.
Figure 7B:
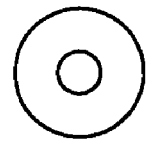
Figure 7C:
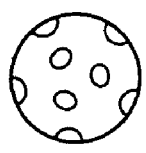
Figure 7D:
Figure 7E:
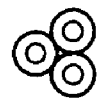

FIGS. 7a-7e illustrate alternative cross-sectional embodiments of the bioabsorbable-radiopaque marker 14 taken through the line 7-7 of FIG. 6. FIG. 7a shows a substantially solid member; FIG. 7b shows a hollow member; FIG. 7c shows a member having pores extending radially into the member; FIG. 7d shows a rectangular or ribbon member; and FIG. 7e shows a braided hollow member. FIG. 7e may also be a substantially solid braided member.

A composite bioabsorbable-radiopaque marker 14 may include a bioabsorbable polymer that is coated, compounded, filled, loaded, or mixed with a radiopaque substance such as iodide, iodine, zirconium oxide, barium sulfate, bismuth trioxide, or a related oxide or salt substance. Composite radiopaque materials may contain at least one element having an atomic number, preferably, higher than about 22. Other radiopaque materials may include gold, platinum, tantalum, metallic biomaterial alloys for coating, and small particles of these materials, preferably, less than 10 microns in size for compounding. For compounding radiopaque constituents and bioabsorbable resins to make extruded bioabsorbable-radiopaque filament, the weight percentage of radiopaque resins to bioabsorbable resins ranges from about 1 percent to about 80 percent. For compounding radiopaque metallic fillers and bioabsorbable resins to make extruded bioabsorbable-radiopaque filament, the weight percentage of radiopaque metallic fillers to bioabsorbable resins ranges from about 1 percent to about 40 percent. The preferred weight percentage of bismuth trioxide and barium sulfate in PLLA filament is a minimum of about 10%. Preferred embodiments of the bioabsorbable-radiopaque marker are set forth below in Table 2.

TABLE 2

| Marker Type | Function | Devices | Preferred Marker Metal Radiopaque Constituents | Metal Radiopaque Constituent Loading, Weight % | Preferred Marker Organic Radiopaque Constituent | Organic Radiopaque Constituent Loading, Weight % | Preferred Marker Matrix Materials For Fast Absorption | Preferred Marker Matrix Materials For Slow Absorption |
|---|---|---|---|---|---|---|---|---|
| threading on helix | mark overall stent length, location in vessel | braided tubular stents, filters, occlusion, valves | Ti, Ta, Zr, Pt | Ti, Zr = 15-40 Ta, Pt - 1-20 | Br, I, Ba, Bi | Br, I = 40-80 Bi, Ba - 10-80 | PGA, polydioxanone | PLLA, PDLA |
| threading around circumference | mark stent ends, location in vessel, covering length, expansion | braided tubular stents, filters, occlusion, valves, stent grafts | Ti, Ta, Zr, Pt | Ti, Zr = 15-40 Ta, Pt = 1-20 | Br, I, Ba, Bi | Br, I = 40-80 Bi, Ba = 10-80 | PGA, polydioxanone | PLLA, PDLA |

TABLE 2-continued

| Marker Type | Function | Devices | Preferred Marker Metal Radiopaque Constituents | Metal Radiopaque Constituent Loading, Weight % | Preferred Marker Organic Radiopaque Constituent | Organic Radiopaque Constituent Loading, Weight % | Preferred Marker Matrix Materials For Fast Absorption | Preferred Marker Matrix Materials For Slow Absorption |
|---|---|---|---|---|---|---|---|---|
| threading on straight axial line | mark overall stent length, location in vessel | braided tubular stents, filters, occlusion, valves, stent grafts | Ti, Ta, Zr, Pt | Ti, Zr = 15-40 Ta, Pt = 1-20 | Br, I, Ba, Bi | Br, I = 40-80 Bi, Ba = 10-80 | PGA, polydioxanone | PLLA, PDLA |
| pigtail rings | mark stent ends or center, location in vessel, expansion | braided tubular stents, filters, occlusion, valves, stent grafts | Ti, Ta, Zr, Pt | Ti, Zr = 15-40 Ta, Pt = 1-20 | Br, I, Ba, Bi | Br, I = 40-80 Bi, Ba = 10-80 | PGA, polydioxanone | PLLA, PDLA |
| coils | mark stent ends or center, location in vessel, expansion | braided tubular stents, filters, occlusion, valves, stent grafts | Ti, Ta, Zr, Pt | Ti, Zr = 15-40 Ta, Pt = 1-20 | Br, I, Ba, Bi | Br, I = 40-80 Bi, Ba = 10-80 | PGA, polydioxanone | PLLA, PDLA |
| knots | mark stent ends or center, location in vessel, expansion | braided tubular stents, filters, occlusion, valves, stent grafts | Ti, Ta, Zr, Pt | Ti, Zr = 15-40 Ta, Pt = 1-20 | Br, I, Ba, Bi | Br, I = 40-80 Bi, Ba = 10-80 | PGA, polydioxanone | PLLA, PDLA |

The column for marker type in Table 2 contains a description of the physical aspects of the marker such as a strand threaded in and out of the braided stent interstices, following a wire helix or in and out of the braided stent interstices around the circumference, or in and out of the braided stent interstices in a straight line in the axial orientation. An interstice is the location where two stent wires in the braid cross over one another. The function of the marker is described in Table 2 to indicate how the marker is used in the endoprosthesis, for example, to indicate the ends of a stent or to allow radiographic visualization of the stent changing from a constrained condition to an expanded condition as it is deployed. A list of devices where the marker could be incorporated is provided in Table 2 and generally contains various types of intralumninal endoprostheses. The preferred metal radiopaque constituents (Ta, Pt, Zr, Ti) are known to be biocompatible and have relatively high atomic numbers and linear attenuation coeffcients. These elements would be added to the bioabsorbable polymer to make the material radiopaque and suitable for radiographic marking. The adjacent column, Metal Radiopaque Constituent Loading, Weight %, indicates the preferred range of loading of the metal radiopaque constituents into the bioabsorbable polymer to make it sufficiently radiopaque, such as from about 1 to about 20 weight percent tantalum or platinum compounded or coated onto the polymer. The same type of information is given in the next two columns for organic radiopaque constituents. The marker may be made with either metal or organic constituents, with metal being preferred for thin markers and organics being more appropriate for thicker markers where higher loadings can be tolerated (so as to not weaken the marker significantly) . The last two columns in the table contain preferred absorbable polymers for the marker matrix material. PLLA and PDLA are preferred for slow-absorbing markers, because the degradation rate of these polymers is rather slow (months to years). PGA and polydioxanone are preferred for fast-absorbing markers because the degradation rate of these polymers is rather fast (weeks to months)

For description purposes, the markers of the invention can be segregated into types; threaded and discrete bioabsorbable-radiopaque markers. A threaded marker is generally a strand or strands of material having radiopacity which is incorporated within the implantable device by interweaving or interbraiding the strand through the struts or wires of the endoprosthesis. A discrete bioabsorbable-radiopaque marker is generally a bioabsorbable-radiopaque polymer strand of material which is securely attached to a localized region of the implantable device and does not significantly extend over a large portion of the device.

An example of a threaded marker in a braided wire tubular stent is a bioabsorbable-radiopaque polymer strand loaded with a radiopaque constituent that is woven in and out of the wire crossing points following the helical path of one individual wire strand in the stent.

An example of a discrete bioabsorbable-radiopaque marker is a coil, knot, or ring of a bioabsorbable-radiopaque polymer strand around a feature of a stent, such as a stent wire crossing point. The strand is wrapped, coiled, or tied around the stent wire and thereby is mechanically attached to the device. The strand ends are clipped off such that the marker is present as a small, tight ring around a feature of the stent. The stent with the attached markers is loaded and deployed from the delivery.

The absorbable radiopaque markers are used in a variety of intraluminal endoprostheses such as stents, grafts, filters, occlusive devices, and valves. The endoprostheses are implanted in airways, the digestive system, and the vascular system. When the markers are implanted and exposed to body fluids the absorbable polymer matrix undergoes degradation and eventually disintegrates releasing the nondegradable radiopaque constituents into the body. If the endoprosthesis and markers have been fully incorporated in the vessel wall, the radiopaque substances will be contained within-the local tissue (as with a stent). If the endoprosthesis and markers are not ingrown and incorporated, the radiopaque substances may be released into the body fluid. The release is of little concern in the digestive system, because the small concentration of particles liberated are likely to have little affect on bile and would be quickly excreted. The release of particles into the vascular system is less desirable but this can be avoided by using low loading percentages and fine particle sizes for vascular device indications.

The function of the absorbable threaded radiopaque marker is to indicate on a radiographic image the location of the stent within the treatment site and the length of the expanded stent can be determined by measuring the length of the marker as it follows the stent shape if the marker was threaded along a stent wire helix or axially along a line in the stent. The marker can be threaded circumferentially at each end of the stent covering in a covered stent or stent-graft to indicate the location of the radiolucent covering material. The stent expansion during deployment can be observed radiographically by watching the radiopaque marker helical or circumferential strand open up as the self-expanding stent is released from its radially constrained state.

Discrete bioabsorbable-radiopaque markers have the same functional purpose as the threaded markers, but they can be more easily used to mark the specific locations of features of interest on the stent. For example, a discrete bioabsorbable-radiopaque marker can be added to the center of the stent length to aid the physician in centering the stent within the stricture. Discrete bioabsorbable-radiopaque markers could be used to attach covering fabrics or films to stents to make stent grafts so that the location of the covering on the stent could be determined radiographically.

The discrete bioabsorbable-radiopaque markers can be made from biocompatible absorbable polymers containing elements with relatively high atomic numbers such as titanium, tantalum, zirconium, and platinum. The radiopaque elements can be added by metallurgically alloying or by making clad composite structures. Radiopaque constituents may be filled into hollow cores, cavities or pores in the polymer matrix. Organic radiopaque powders containing elements or salts or oxides of elements such as bromine, iodine, iodide, barium, and bismuth could be used instead of metal powders.

The amount of radiopaque constituent that is added to the absorbable polymer matrix is generally from about 1-80 weight percent, but the specific loading depends upon the atomic number of the radiopaque constituent and the thickness of the marker. Metallic elements like tantalum and platinum which have high atomic numbers can be loaded in small percentages (about 1-20 weight percent) while metallic elements with lower atomic numbers such as titanium and zirconium have to be loaded in higher percentages (about 20-40%). Organic radiopaque constituents with relatively low atomic numbers like iodine and bromine require loading percentages of from about 40-80 weight percent while organics with higher atomic numbers could be as low as 10% in thick markers. It is desirable to have the radiopaque constituent particle size be less than 10 microns so that when dispersed into the body the particles will not be so large as to cause obstruction or embolization.

EXAMPLE 1

An absorbable threaded radiopaque marker can be in the form of a strand of poly ($\alpha$-hydroxy acid) polymer containing radiopaque elements, oxides, or salts of elements with atomic numbers of from about 22 to about 83 interwoven or interbraided along a helical, circumferential, or axial orientation on an endoprosthesis such as a stent, stent-graft, graft, filter, occlusive device, and valve. The radiopaque material has a linear attenuation coefficient of from about 5.46 cm$^{-1}$ at 50 KeV to about 151.53 cm$^{-1}$ at 50 KeV.

EXAMPLE 2

An absorbable threaded radiopaque marker can be in the form of a strand of poly ($\alpha$-hydroxy acid) polymer containing radiopaque elements, oxides, or salts of elements with atomic numbers of from about 22 to about 83 disposed on one or more surfaces of an endoprosthesis such as a stent, stent-graft, graft, filter, occlusive device, and valve. The radiopaque material has a linear attenuation coefficient of from about 5.46 cm$^{-1}$ at 50 KeV to about 151.53 cm$^{-1}$ at 50 KeV.

EXAMPLE 3

An absorbable threaded radiopaque marker can be in the form of a strand of poly ($\alpha$-hydroxy acid) polymer containing radiopaque elements with atomic numbers of from about 22 to about 83, loaded into hollow cores, cavities, or pores of the polymer portion and disposed on an endoprosthesis such as a stent, stent-graft, graft, filter, occlusive device, and valve. The radiopaque material has a linear attenuation coefficient of from about 5.46 cm$^{-1}$ at 50 KeV to about 151.53 cm$^{-1}$ at 50 KeV.

EXAMPLE 4

An absorbable threaded radiopaque can be a coated or clad composite marker strand of poly ($\alpha$-hydroxy acid) polymer and radiopaque metallic elements with atomic numbers of from about 22 to about 83, preferably titanium, tantalum, zirconium, and disposed on an endoprosthesis such as a stent, stent-graft, graft, filter, occlusive device, and valve. The radiopaque material has a linear attenuation coefficient of from about 5.46 cm$^{-1}$ at 50 KeV to about 94.95 cm$^{-1}$ at 50 KeV.

EXAMPLE 5

An absorbable threaded radiopaque marker can be in the form of a strand of poly ($\alpha$-hydroxy acid) polymer monofilament, ribbon, or multifilament wire containing radiopaque metallic elements with atomic numbers of from about 22 to about 83, preferably compounded or coated with titanium, tantalum, zirconium; and platinum metal powders or bromine, iodine, iodide, barium, and bismuth element, oxides or salts disposed on an endoprosthesis such as a stent, stent-graft, graft, filter, occlusive device, and valve. The radiopaque material has a linear attenuation coefficient of from about 5.46 cm$^{-1}$ at 50 KeV to about 149.08 cm$^{-1}$ at 50 KeV.

EXAMPLE 6

An absorbable threaded radiopaque marker can be in the form of poly ($\alpha$-hydroxy acid) polymer matrix composite strand containing radiopaque metallic elements with atomic numbers of from about 22 to about 83, preferably titanium, tantalum, zirconium, and platinum metal powders or bromine, iodine, iodide, barium, and bismuth element, oxides or salt powders disposed on an endoprosthesis such as a stent, stent-graft, graft, filter, occlusive device, and valve. The radiopaque material has a linear attenuation coefficient of from about 5.46 cm$^{-1}$ at 50 KeV to about 149.08 cm$^{-1}$ at 50 KeV.

EXAMPLE 7

A discrete bioabsorbable-radiopaque marker can be in the form of poly ($\alpha$-hydroxy acid) polymer containing radiopaque metallic elements with atomic numbers of from about 22 to about 83, preferably titanium, tantalum, zirconium, and platinum attached by wrapping, coiling, or tying around features within an endoprosthesis such as a stent, stent-graft, graft, filter, occlusive device, and valve such that the marker is attached and bioabsorbably removable from the endoprosthesis. The radiopaque material has a linear attenuation coefficient of from about 5.46 cm$^{-1}$ at 50 KeV to about 149.08 cm$^{-1}$ at 50 KeV.

Figure 8A:
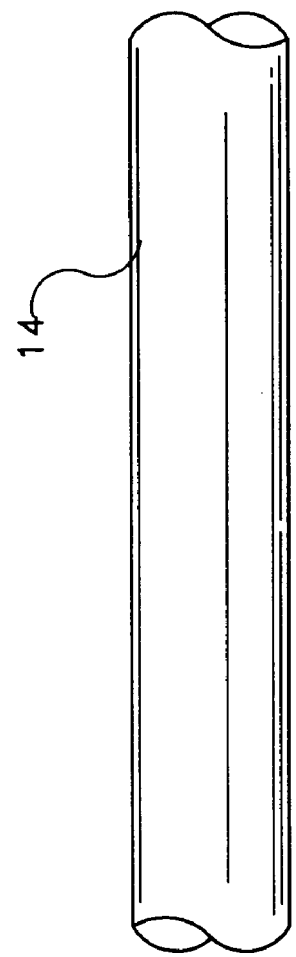
FIGS. 8a-8c are side views of three alternative bioabsorbable-radiopaque markers.
Figure 8B:
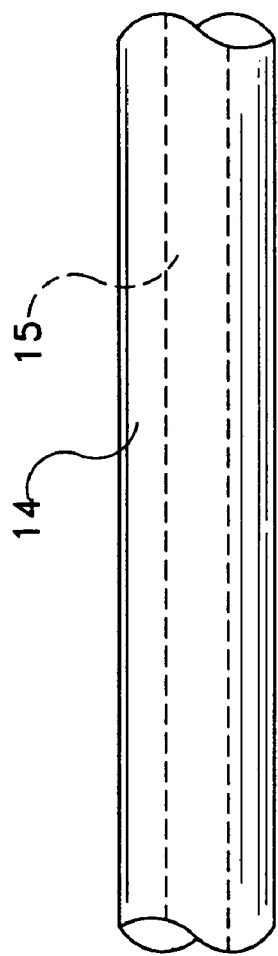
Figure 8C:
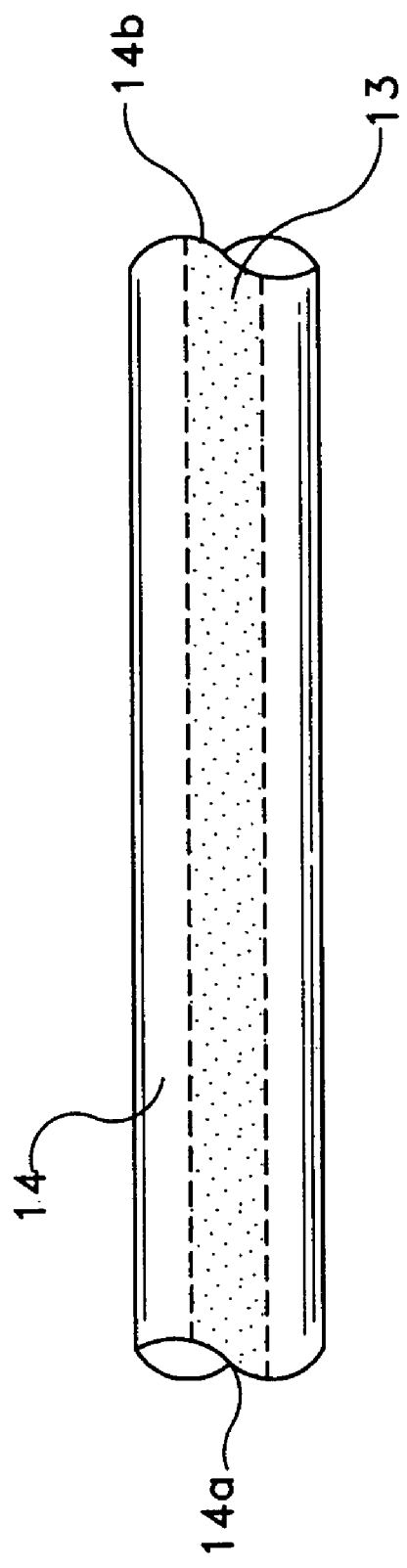

Reference is made to FIGS. 8a-8c illustrating alternative embodiments of a portion of a bioabsorbable-radiopaque marker 14. The bioabsorbable-radiopaque marker 14 may have at least one portion for temporary containment of a radiopaque material. The radiopaque material may be disposed in one or more hollow, cavity or pope portions in the marker 14. For example, FIG. 8a shows a solid bioabsorbable-radiopaque marker 14. As shown in FIGS. 8b-8c, the bioabsorbable-radiopaque marker 14, may receive a radiopaque core 13 disposed in the once hollow 15 portion. The radiopaque core 13 may be slowly released from the open ends 14a, 14b of the hollow portion 15 into the body. Alternatively, the radiopaque core 13 may be released from the radiopaque core 13 through pores in the walls of the marker 14 into the body.

Figure 9:
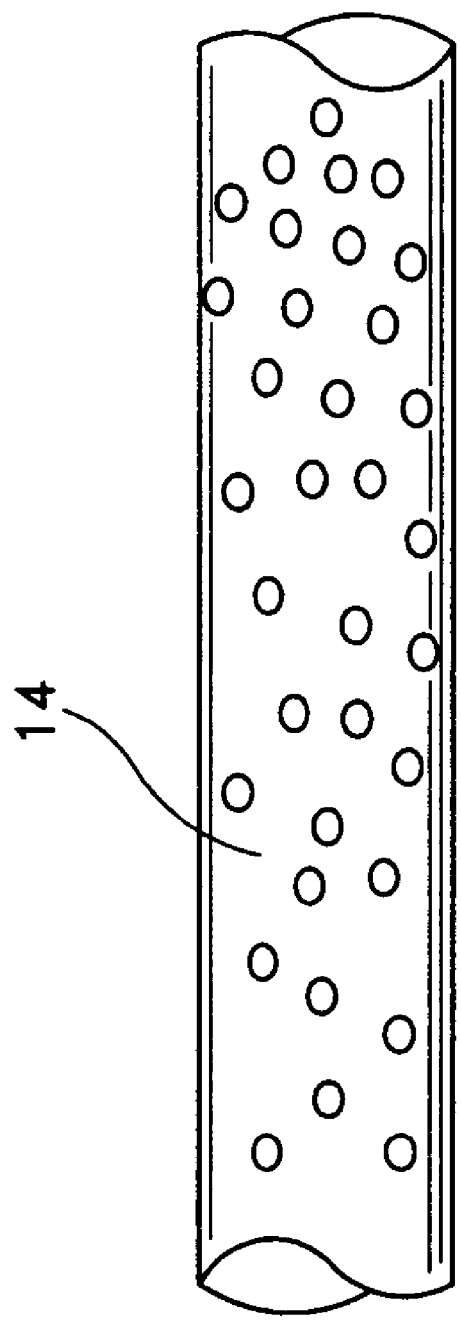
FIG. 9 is a side views of a porous bioabsorbable-radiopaque marker.

FIG. 9 is an illustration of a bioabsorbable-radiopaque marker 14 having pores 35. The pores may connect to a reservoir of radiopaque material in a cavity 25 or hollow 15 area or the individual pores 35 may be filled with radiopaque material. The pores 35 allow the radiopaque material disposed in the marker 14 to exit from the marker 14 over a period of time.

The radiopaque material may be solid or include a bioabsorbable casing surrounding a liquid, solid, gel, powder, or combination thereof and be held in place in a hollow portion 15, cavity 25, or porous 35 portion by a relatively weak bioabsorbable adhesive, bioabsorbable gelatin, friction, or by other mechanical-or chemical means known in the art. The radiopaque material may be designed to disperse from the bioabsorbable-radiopaque marker 14 after a predetermined period of time. The radiopaque material preferably has at least one element with an atomic number of from about 22 to about 83 and is removably-attachable in at least one hollow 15, cavity 25, or porous 35 portions in the marker 14. The bioabsorbable-radiopaque marker 14 may further comprise one or more walls 30 including walls between hollow 15, cavity 25, and porous 35 portions, proximal and distal walls, and combinations thereof that are adapted to bioabsorb in vivo.

Figure 10A:
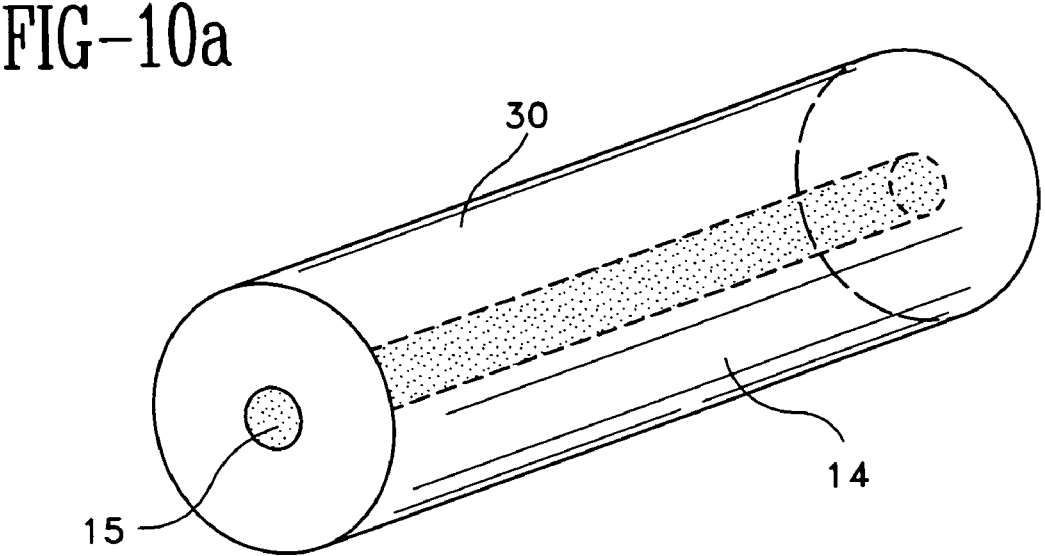
Figure 10B:
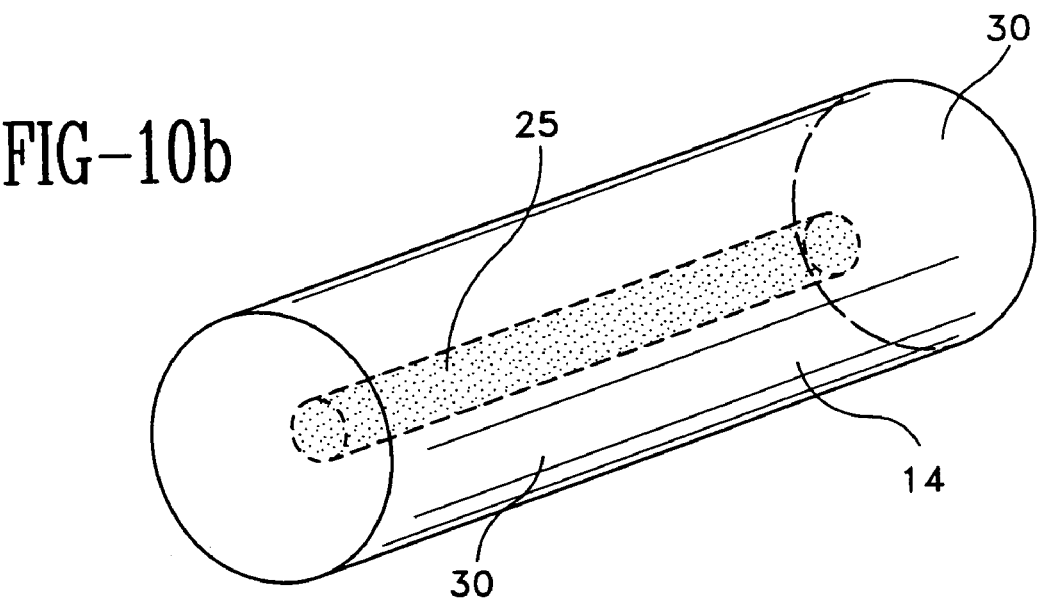

Reference is made to FIGS. 10a-10d illustrating different embodiments of the bioabsorbable-radiopaque marker 14 having hollow 15, cavity 25, porous 35 portions, or combinations thereof filled with a non-toxic radiopaque material. FIG. 10a shows a bioabsorbable-radiopaque marker 14 with a hollow 15 portion filled with radiopaque material and having at least one of the proximal or distal ends open; FIG. 10b shows a bioabsorbable-radiopaque marker 14 with a cavity 25 portion filled with radiopaque material having closed ends; FIG. 10c shows a bioabsorbable-radiopaque marker 14 with porous 35 portions filled with radiopaque material; and FIG. 10d shows a bioabsorbable-radiopaque marker 14 with combinations of hollow 15, cavity 25, and porous 35 portions filled with radiopaque material. The bioabsorbable-radiopaque marker 14 reacts with body fluids and decomposes and then the constituents are absorbed or excreted from the body.

FIG. 11 illustrates discrete bioabsorbable-radiopaque markers 14 made by forming small rings or coils of bioabsorbable-radiopaque filament around features of the implantable endoprosthesis 16. Relatively small and discrete filament loops (pigtail) bioabsorbable-radiopaque markers 14 are shown at the wire crossing points on the tubular braid.

Figure 12:
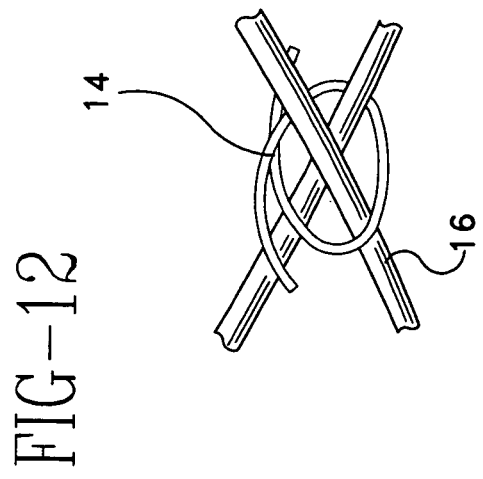
FIG. 12 is the detail bounded by the dashed-line circle in FIG. 12 illustrating a bioabsorbable-radiopaque marker disposed around one implantable endoprosthesis wire crossing point.
Figure 14:
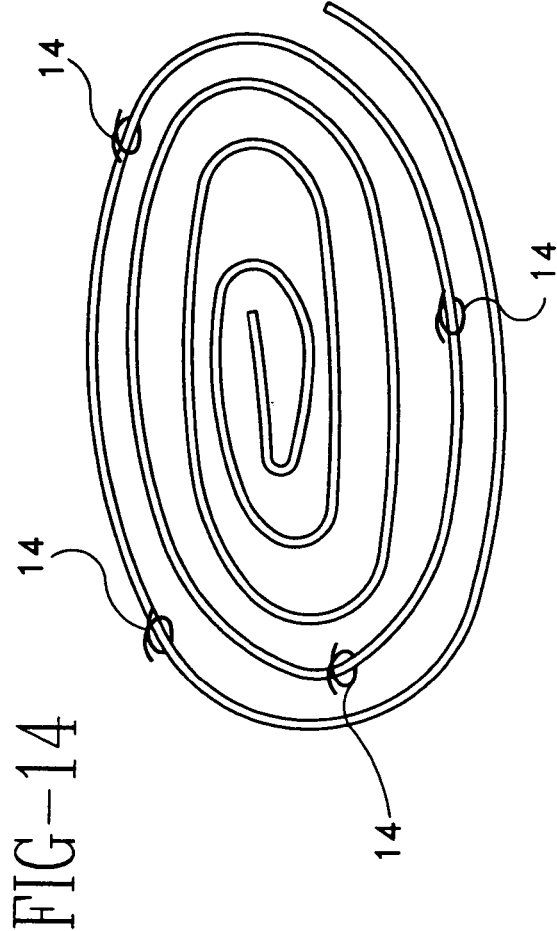
FIG. 14 illustrates the discrete bioabsorbable-radiopaque marker positioned on an embolization occlusion coil intravascular device.

FIG. 12 illustrates the detail bounded by the dashed-line circle in FIG. 11 showing a bioabsorbable-radiopaque marker 14 around one implantable endoprosthesis 16 wire crossing point.

Figure 13:
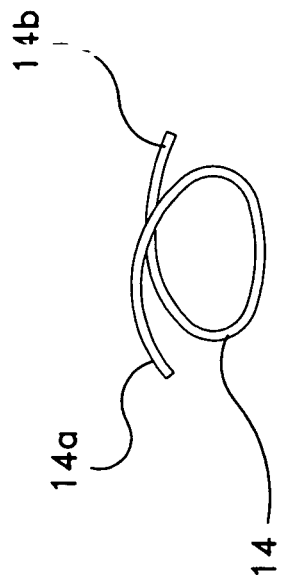
FIG. 13 is a side view illustrating a discrete radiopaque marker.

FIG. 13 illustrates the bioabsorbable-radiopaque marker 14 of FIG. 12 and FIG. 13 and shows filament ends 14a, 14b which simply pass over each other to form an enclosed loop that is further preferably knotted, twisted, or tied at ends 14a, 14b. The bioabsorbable-radiopaque markers 14 may be relatively small and comprise a single loop or pigtail of filament around one filament crossing point, filament, an embolization coil, or the like. The bioabsorbable-radiopaque marker 14 is preferably made of a PGA, Polydioxanone, PLLA, PDLA, or combinations thereof. Biocompatible radiopaque metal constituents preferably include titanium, zirconium, tantalum, and platinum. Preferred organic radiopaque constituents include bromine, barium, bismuth, iodine, or combinations thereof The bioabsorbable-radiopaque marker 14 is preferably formed from an elongate member such as a filament and shaped accordingly onto the implantable endoprosthesis 16. The bioabsorbable-radiopaque marker 14 advantageously allows custom molding of the implantable endoprosthesis 16 without the need to acquire preformed marker bands or to devise a complicated manufacturing operation. The bioabsorbable-radiopaque markers 14 may be easily and quickly added to the implantable endoprosthesis 16. Also, only small, specific sites are marked by the bioabsorbable-radiopaque marker 14 so a minimum amount of foreign body material would be added to the implantable endoprosthesis 16.

The bioabsorbable-radiopaque markers 14 should preferably be smaller than the size of the element in the implantable endoprosthesis 16. A smaller diameter bioabsorbable-radiopaque marker 14 should fit through most weaves, be deformable, and may be cut to size.

Reference is made to FIGS. 12-13 illustrating discrete bioabsorbable-radiopaque markers 14 looped one or more times about a filament or filament crossing point to prevent release therefrom. The ends 14a, 14b are clipped and positioned to lie in a plane parallel to the longitudinal axis of the implantable endoprosthesis 16. The bioabsorbable-radiopaque marker 14 may be disposed on one or more filament crossing or every other filament crossing point around the circumference of the braid in one circular transverse plane. The bioabsorbable-radiopaque markers 14 may be positioned to form one or more circumferential rings on the implantable endoprosthesis 16. Alternatively, the bioabsorbable-radiopaque markers 14 may be positioned along an embolization occlusion coil intravascular device or. filament at predetermined locations as illustrated in FIG. 15. The ends 14a, 14b may then be tied, twisted, knotted, or adhesively connected together and thereafter clipped and positioned to lie in an unobtrusive low-profile position.

It will be evident from considerations of the foregoing that the bioabsorbable-radiopaque marker 14 may be constructed using a number of methods and materials, in a wide variety of sizes and styles for the greater efficiency and convenience of a user.

A bioabsorbable marker that may advantageously be used in conjunction with the present invention is disclosed in J. Stinson's and Claude Clere's U.S. patent application No.

entitled "Radiopaque Markers And Methods Of Using Same", Ser. No. 08/905,821 (now U.S. Pat. No. 6,340,367), filed concurrently herewith, and commonly assigned to the assignee of this application.

A bioabsorbable stent that may advantageously be used in conjunction with the present invention is disclosed in J. Stinson's U.S. patent application Ser. No. entitled "Bioabsorbable Implantable Endoprosthesis With Reservoir And Method Of Using Same", Ser. No. 08/905,806 (now U.S. Pat. No. 5,980,564), filed concurrently herewith, and commonly assigned to the assignee of this application.

Another bioabsorbable stent that may advantageously be used in conjunction with the present invention is disclosed in J. Stinson's U.S. patent application Ser. No entitled "Bioabsorbable Self-Expanding Stent", Ser. No. 08/904,467 (now U.S. Pat. No. 6,245,103), filed concurrently herewith, and commonly assigned to the assignee of this application.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

The invention claimed is:

1. An implantable prosthesis and bioabsorbable radiopaque marker system comprising:
   an implantable, tubular, axially flexible prosthesis including a plurality of elongate filaments interwoven in a braided configuration, adapted for delivery to a treatment site in a body lumen, wherein the elongate filaments form multiple crossing points, and
   a radiopaque marker comprising a bioabsorbable material and a radiopaque material and adapted to degrade in vivo whereby the bioabsorbable material is capable of being metabolized through the body, and the radiopaque material is excreted from or stored in the body; and
   wherein the radiopaque marker is more radiopaque than the prosthesis, and is secured with respect to the prosthesis in surrounding relation to a pair of the elongate filaments at one of the crossing points and in a manner to enable locating the prosthesis in vivo by fluoroscopically imaging the marker.

2. The system of claim 1 wherein:
the bioabsorbable material comprises a material selected from the group consisting of: poly-L-lactide, poly-D-lactide, polyglycolide, polydioxanone, polycaprolactone, polygluconate, polylactic acid-polyethylene oxide copolymers, modified cellulose, collagen, poly-(hydroxybutyrate), polyanhydride, polyphosphoester, poly (amino acids), poly(alpha-hydroxy acid), and combinations thereof.

3. The system of claim 1 wherein:
the radiopaque material consists of a material selected from the group consisting of: barium sulfate, bismuth trioxide, bromine, iodine, iodide, titanium oxide, zirconium oxide, tantalum, and combinations thereof.

4. The system of claim 1 wherein:
the radiopaque material consists of an oxide or a salt.

5. The system of claim 1 wherein:
the marker incorporates the radiopaque material at from about 1 to about 80 weight percent.

6. The system of claim 1 wherein:
the bioabsorbable material consists of PLLA, and the radiopaque material consists of bismuth trioxide at least about 10 weight percent.

7. The system of claim 1 wherein:
the bioabsorbable material consists of PLLA, and the radiopaque material consists of barium sulfate at least about 10 weight percent.

8. The system of claim 1 wherein:
the bioabsorbable material consists of polylactide, and the radiopaque material consists of a material selected from the group consisting of: barium sulfate, bismuth trioxide, iodine, iodide, and combinations thereof.

9. The system of claim 1 wherein:
the bioabsorbable material consists of a material selected from the group consisting of poly-L-lactide, poly-D-lactide, polyglycolide, and combinations thereof and the radiopaque material consists of a material selected from the group consisting of: barium sulfate, bismuth trioxide, bromine, iodine, iodide, and combinations thereof.

10. The system of claim 1 wherein:
the bioabsorbable material consists of a material selected from the group consisting of: polyglycolide, polygluconate, polydioxanone, and combinations thereof and the radiopaque material consists of a material selected from the group consisting of: barium sulfate, bismuth trioxide, bromine, iodine, iodide, and combinations thereof.

11. The system of claim 1 wherein:
the radiopaque marker is in a form selected from the group consisting of: mono-filament, multi-filament, thread, ribbon, suture, and combinations thereof.

12. The system of claim 1 wherein:
the marker further comprises at least one cavity containing the radiopaque material.

13. The system of claim 1 wherein:
the radiopaque marker further comprises a radiopaque filament interwoven with the elongate filaments of the prosthesis.

14. The system of claim 1 wherein:
the radiopaque marker further comprises a radiopaque filament smaller in diameter than the elongate filaments of the prosthesis.

15. The system of claim 1 wherein:
the radiopaque marker is secured to the prosthesis with an adhesive.

16. An implantable endoprosthesis and bioabsorbable-radiopaque marker system comprising:
   an implantable expandable tubular prosthesis formed of a plurality of elongate filaments interconnected with one another, the prosthesis adapted to be disposed in a body lumen; and
   an elongated marker adapted to be secured with respect to the prosthesis in a manner to enable locating the prosthesis in vivo by fluoroscopically imaging the marker, said marker comprising a bioabsorbable material and a radiopaque material, the marker having at least one cavity with the radiopaque material disposed therein and wherein the bioabsorbable material at least partially contains the radiopaque material, wherein the marker is more radiopaque than the prosthesis.

17. The system of claim 16 wherein:
the elongate filaments are interbraided with one another.

18. The system of claim 16 wherein:
the marker comprises a filament incorporating the bioabsorbable material and the radiopaque material, interwoven with the elongate filaments of the prosthesis.

19. The system of claim 16 wherein:

the elongate filaments of the prosthesis form multiple crossing points, and the radiopaque marker is secured in surrounding relation to a pair of the elongate filaments at one of the crossing points.

20. The system of claim 16 wherein:

the radiopaque marker comprises a radiopaque filament smaller in diameter than the elongate filaments of the prosthesis.

21. An implantable medical device, including:

a tubular, radially expandable prosthesis adapted for deployment in vivo, wherein the prosthesis includes a plurality of elongate filaments forming a plurality of crossing points; and a discrete marker comprising an interwoven elongate filament, including a dispersible radiopaque material and thereby being more radiopaque than the prosthesis, and further including a bioabsorbable material whereby the marker is degradable in vivo;

wherein the discrete marker is secured to the prosthesis in a surrounding relationship to a pair of the elongate filaments at one of the crossing points at a predetermined portion of the prosthesis to provide an enhanced radiopacity over said predetermined portion, thus to facilitate a selective positioning of the prosthesis in vivo through a fluoroscopic imaging of the marker; and wherein the discrete marker degrades in vivo at a first degradation rate, thus to diminish the radiopacity over said predetermined portion after deployment.

22. The device of claim 21 wherein:

the filaments are interwoven in a braided configuration.

23. The device of claim 22 wherein:

the discrete marker further comprises an elongate element interbraided with the elongate filaments.

24. The device of claim 21 wherein:

the prosthesis is degradable, and the prosthesis degrades in vivo at a second degradation rate lower than the first degradation rate.

25. The device of claim 21 wherein:

the bioabsorbable material comprises a material selected from the group consisting of: poly-L-lactide, poly-D-lactide, polyglycolide, polydioxanone, polycaprolactone, polygluconate, polylactic acid-polyethylene oxide copolymers, modified cellulose, collagen, poly-(hydroxybutyrate), polyanhydride, polyphosphoester, poly (amino acids), poly(alpha-hydroxy acid), and combinations thereof.

26. The device of claim 21 wherein:

the radiopaque material comprises a material selected from the group consisting of: barium sulfate, bismuth trioxide, bromine, iodine, iodide, titanium oxide, zirconium oxide, tantalum, and combinations thereof.

27. The device of claim 21 wherein:

the bioabsorbable material consists essentially of polylactide, and the radiopaque material comprises a material selected from the group consisting of: barium sulfate, bismuth trioxide, iodine, iodide, and combinations thereof.

28. The device of claim 21 wherein:

the bioabsorbable material comprises a material selected from the group consisting of poly-L-lactide, poly-D-lactide, polyglycolide, and combinations thereof and the radiopaque material comprises a material selected from the group consisting of: barium sulfate, bismuth trioxide, bromine, iodine, iodide, and combinations thereof.

29. The device of claim 21 wherein:

the bioabsorbable material comprises a material selected from the group consisting of: polyglycolide, polygluconate, polydioxanone, and combinations thereot and the radiopaque material comprises a material selected from the group consisting of: barium sulfate, bismuth trioxide, bromine, iodine, iodide, and combinations thereof 30. The device of claim 21 wherein:

the marker further comprises at least one cavity containing the radiopaque material.

* * * * *

UNITED STATES PATENT AND TRADEMARK OFFICE
CERTIFICATE OF CORRECTION

PATENT NO. : 7,553,325 B2
APPLICATION NO. : 10/635114
DATED : June 30, 2009
INVENTOR(S) : Jonathan S. Stinson It is certified that error appears in the above-identified patent and that said Letters Patent is hereby corrected as shown below:

Column 18, Claim 9, Line 14: delete "thereof" and insert --thereof;--.

Column 18, Claim 10, Line 21: delete "thereof" and insert --thereof;--.

Column 20, Claim 25, Lines 6-7: delete "poly-(hydroxybutyrate)," and insert --poly(hyroxybutyrate),--.

Column 20, Claim 29, Line 35: delete "thereof" and insert --thereof.--.

Signed and Sealed this

Twenty-third Day of November, 2010

David J. Kappos
*Director of the United States Patent and Trademark Office*